(12) United States Patent
Drew et al.

(10) Patent No.: US 8,783,566 B1
(45) Date of Patent: Jul. 22, 2014

(54) ELECTRONIC REGISTRATION KIOSK FOR MANAGING INDIVIDUAL HEALTHCARE INFORMATION AND SERVICES

(76) Inventors: Norman J. Drew, Lakeland, FL (US); James Owen Childers, Freeland, WA (US); Jeff Lee, Lake Worth, FL (US)

( * ) Notice: Subject to any disclaimer, the term of this patent is extended or adjusted under 35 U.S.C. 154(b) by 54 days.

(21) Appl. No.: 13/493,147

(22) Filed: Jun. 11, 2012

Related U.S. Application Data

(60) Provisional application No. 61/496,654, filed on Jun. 14, 2011.

(51) Int. Cl.
*G06K 7/00* (2006.01)

(52) U.S. Cl.
USPC ............................. 235/382; 235/375; 235/380

(58) Field of Classification Search
USPC .................................. 235/375, 380, 382, 385
See application file for complete search history.

(56) References Cited

U.S. PATENT DOCUMENTS

| | | | |
|---|---|---|---|
| 8,212,675 B2 | 7/2012 | Page | |
| 2005/0099766 A1* | 5/2005 | Fraley et al. | 361/685 |
| 2006/0249576 A1* | 11/2006 | Nakada et al. | 235/382 |
| 2009/0166375 A1* | 7/2009 | Butler et al. | 221/282 |
| 2009/0250515 A1* | 10/2009 | Todd et al. | 235/383 |

* cited by examiner

*Primary Examiner* — Matthew Mikels
(74) *Attorney, Agent, or Firm* — H. John Rizvi; Gold & Rizvi P.A.

(57) ABSTRACT

The present invention provides a registration kiosk for use in managing individual healthcare services and information. The electronic registration kiosk provides access control to healthcare information stored on medical smart cards by including biometric authentication, includes a high definition camera for capturing images, and provides a large interactive touch screen. The electronic registration kiosk comes in a variety of different models including different floor kiosks, and a wall-mountable kiosk. Individuals can access a registration kiosk to apply for a medical smart card, print medical directive forms, and/or request prescription refills and receive confirmation via, text or email when the prescription is ready.

19 Claims, 4 Drawing Sheets

ELECTRONIC REGISTRATION KIOSK FOR MANAGING INDIVIDUAL HEALTHCARE INFORMATION AND SERVICES

CROSS-REFERENCE TO RELATED APPLICATION

This application claims the benefit of U.S. Provisional Patent Application Ser. No. 61/496,654 filed Jun. 14, 2011, which is incorporated herein in its entirety.

FIELD OF THE INVENTION

The present disclosure relates generally to electronic kiosks. More particularly, the present disclosure relates to an electronic registration kiosk for managing individual healthcare services and information. The electronic registration kiosk provides access control to healthcare information stored on medical smart cards by including biometric authentication, includes a high definition camera for capturing images, and provides a large interactive touch screen. The electronic registration kiosk comprises a variety of models including different floor kiosks, and a wall-mountable kiosk. Individuals can access any of the registration kiosks to apply for a medical smart card, print medical directive forms, and/or request prescription refills and receive confirmation via, text or email when the prescription is ready.

BACKGROUND OF THE INVENTION

Electronic or interactive kiosks are exhibits that generally include a computer system that is operated to provide access to applications and information relating to various industries, businesses, or public and private welfare. Typically, the computer system is securely housed within the electronic kiosk and includes software for providing application programs, and hardware that includes an electronic display and a plurality of keys for inputting data and navigating through application programs. Most electronic kiosks are located in high traffic settings where individuals often congregate such as in banks, hotels, airports, malls, universities and department stores, to name a few.

Electronic kiosks come in a variety of different forms. The structural framework of most kiosks consists generally of plastic, wood, metal, or any combination thereof. Floor kiosks provide a popular style of electronic kiosk that includes a structural housing defined by sidewalls, a back panel, a front panel and a top member. A computer system is safely stored within the housing of the kiosk, and an electronic display screen and input keys are disposed in a central region of the kiosk to provide easy, accessible use. Other conventional kiosks include kiosks that are designed for mobility, where the kiosk is easily transportable from one location to another. Still other kiosks comprise wall-mounted kiosks that are securely fitted in the walls of buildings. Wall-mounted kiosks provide the convenience of requiring less floor space, and are often smaller in size.

Electronic kiosks find use in diverse applications. For example, electronic kiosks are often used for entertainment or educational purposes. Such kiosks allow individuals to interact with application programs for viewing movies, determining times and dates of shows, concerts or events, accessing bulletin boards, reviewing classifications, learning about possible seminars, programs or classes, or providing access to an abundance of information. Electronic kiosks also play a vital role in commerce. Such kiosks often include card readers that are designed to interface with credit cards, bank cards, and charge cards. Electronic kiosks can be used to make purchases, pay bills, or transact business. Electronic kiosks are also used by individuals to manage banking accounts, withdraw funds, make deposits, and apply for credit. Some kiosks are incorporated in appliances and used to pay for goods. For example, electronic kiosks also find use in gas pumps where individuals use charge cards to pay for gas, and in vending machine applications.

Few electronic kiosks have been designed for use in the medical industry. Most kiosks include computer systems that allow professionals to access medical information pertaining to scholarly teachings, medical procedures, medical product information, government warnings, studies, and information relating to medication. Alternative forms of kiosks have been designed for interfacing with information storage cards. For example, cards including bar codes or magnetic stripe cards are often used to store individual medical information. Kiosks have been adapted to include magnetic head readers and bar code readers to read information stored on the medical cards. One drawback however of such systems is that the bar code card and magnetic stripe card provide poor security and compromise a patient's privacy and security of information. To address the security drawbacks of the prior art cards, smart cards have been developed to provide greater security access to information stored on the smart card, and to store more information on the smart card. With advancement in storage information technology, electronic kiosks have been adapted for use with such smart cards. Conventional electronic kiosks include input keys and an electronic display to navigate through information and data, and to view information stored on smart cards.

Although prior art kiosk systems have been designed for use with smart cards, such kiosk systems suffer from certain drawbacks. For example, traditional electronic kiosks only permit individuals to view information stored on storage cards. Individuals using conventional kiosks do not have the ability to fully manage medical healthcare services such as making appointments, acquiring medical directive forms, or requesting prescription refills and receiving confirmation. Individuals lack the autonomy in managing their own medical healthcare information. In many situations, medical service providers often conduct a medical intake of individuals and then record the solicited information on a computer or in a hard copy file. The medical intake typically involves a number of questions that are presented to individuals. The process can be uncomfortable at times and place the interviewee in an awkward position. Some individuals may wish that certain vital healthcare information remain private and viewable only to certain individuals, such as a physician. Individuals feel less intimidated when interacting directly with an electronic kiosk in fully managing their healthcare.

Another drawback of conventional electronic kiosks used in the medical industry is that they do not provide the convenience and ability of applying for and acquiring a medical smart card at any time and in various locations. Most conventional kiosk systems require an individual to visit a medical service provider at an office or clinic, during business hours, to either apply for limited use medical card or to acquire an application to be filled out at a later time. The person is obligated to make an appointment with a medical clinic or office and subsequently travel to the healthcare facility or clinic, or to make arrangements via, mail. Many individuals may wish to manage healthcare information and services outside the confines of a doctor's office, and preferably at a location the individual feels more comfortable in or is frequented more often, such as at a pharmacy, a mall or at the bank. Also, traditional kiosks do not provide immediate access to certain forms like medical directives. Individuals may wish to use an electronic kiosk to acquire such forms. Finally, conventional kiosks often lack the requisite security when interfacing with external storage devices like smart cards. Many kiosks include the use of passwords or personal identification numbers that are needed to gain access to information stored on the cards. However, the use of passwords and personal identification numbers alone provides limited security in managing individual healthcare information.

What is desired is an electronic kiosk for use with medical smart cards in managing healthcare information and services that provides secure, access control by including biometric authentication, provides immediate access to a variety of medical directive forms, and is accessible to request a medical smart card, and/or prescription refills. The medical smart card is used for storing medical information and providing vital life-saving information to medical service providers in the event of an emergency.

SUMMARY OF THE INVENTION

A first aspect of the present invention provides, a registration kiosk comprising: an exhibit housing a computer system and system devices, said computer system including a processor and a memory and electrically communicating with said system devices where the system devices include; an interactive touch screen; a first printer for printing receipts, and a second printer for printing healthcare related forms, where the first printer is associated with a first printer slot, and the second printer is associated with a second printer slot; a card reader system selectively interfacing with medical smart cards including healthcare information stored on said cards, and credit cards; a biometric authentication system including a biometric sensor for capturing biometric signatures; a high definition camera system operated to capture images of individuals using the kiosk; a keyboard, and, wherein the registration kiosk is used to manage healthcare information or services including applying for a medical smart card, printing medical directive forms, and requesting prescription refills.

A second aspect of the registration kiosk further includes an audio system that is electrically coupled to the computer system and includes one or more speakers associated with speaker holes that are provided in a front area of the exhibit. The registration kiosk also includes wireless technology including any one of 2G, 3G, 4G, 5G, Wi-Fi, WiMax or Blue Tooth technology, an input/output (I/O) interface situated about the exhibit and including at least one of a universal serial bus (USB) port, an Ethernet port, a TTL port, a serial and parallel port, modem connections, cable connections or telephone line connections.

In another aspect, the registration kiosk further includes a handicapped audio access port, where the audio access port is electrically coupled to the computer system for providing audible information, data or instructions, and further including a trackball located adjacent the keyboard, a ventilation system, and a backup power supply.

In yet another aspect, the biometric sensor includes any one of a fingerprint sensor, a palm sensor, a speech recognition system, or a retinal validation sensor, and wherein the biometric authentication system further includes a biometric signature database including biometric signatures associated with a plurality of individuals authorized to use the registration kiosk. The healthcare information includes an individual's demographic and profile information, medical emergency contact information, physician/specialist information, medical conditions, procedural medical history, information relating to prescription and over-the-counter medicine, vitamins or supplements, vaccination or immunization historical records, advance directives, medical insurance information, and a photograph of an individual owner of said medical smart card. The healthcare related forms include any of service agreements, authorizations to treat, advanced directives, immunization forms, privacy statements, laws and rules, a power of attorney, and a living will.

In another aspect, the exhibit includes a base, two vertical sidewalls extending upwards from the base, a central panel, a front panel, a lateral shelf, and a rear panel, wherein the central panel is setback a distance from front longitudinal edges of the sidewalls to define a zone of privacy, and wherein the biometric sensor, the audio access port, a card reader slot and the first printer slot are disposed on or in the central panel between the two vertical sidewalls.

In yet another aspect, the exhibit includes a table having a left support and a right support, where the table is attached to a vertically adjustable column, where the vertically adjustable column includes a base for supporting the kiosk on a horizontal surface, and where the keyboard is disposed between the supports.

In another aspect, the exhibit includes a wall-mountable kiosk having a faceplate with an opening to provide access to the interactive touch screen, where the keyboard includes a plurality of keys situated about the face plate.

In yet another aspect, there is provided, a method of registering for a medical smart card, and managing healthcare information and services comprising: providing a registration kiosk comprising: an exhibit housing a computer system and system devices, where the computer system includes a processor and a memory and electrically communicates with the system devices, where the system devices include; an interactive touch screen; a first printer for printing receipts, and a second printer for printing healthcare related forms, the first printer associated with a first printer slot, and the second printer associated with a second printer slot; a card reader system selectively interfacing with medical smart cards including healthcare information stored on the cards, and credit cards; a biometric authentication system including a biometric sensor for capturing biometric signatures; a high definition camera system operated to capture images of individuals using the registration kiosk; and a keyboard.

In one aspect, the method includes the steps of operating an application server hosting medical service application software associated with managing individual healthcare information and services, where the registration kiosk electrically communicates with the application server over a wired or wireless network; capturing an image with the high definition camera of an individual using the registration kiosk and processing a biometric signature of an individual user; and receiving information from an individual user to register for a medical smart card, and storing the received information on the medical smart card upon successful completion of a registration process, or selectively interfacing a medical smart card with the card reader system of the registration kiosk to view and manage healthcare information and services when the biometric signature of the individual user is authenticated.

In yet another aspect, the method further includes the steps of receiving a request for prescription refills of medication, and sending a text or email message confirming readiness of said refills; processing a biometric signature of an individual user includes the step of reading a biometric fingerprint signature of the user when the user places a finger on the biometric sensor. A step also includes entering personal information, or entering personal information and medical information, and paying a predetermined fee with a credit card to complete the registration process. A step also includes printing a receipt via, the first printer, and printing healthcare related forms via, the second printer, where the receipt and the healthcare related forms are forwarded through a corresponding slot.

In another aspect, there is provided an electronic kiosk for managing healthcare information and services, where the electronic kiosk comprises: a structure housing a computer system having a memory and a processor and including: an interactive touch screen; a first printer for printing receipts, and a second printer for printing healthcare related forms; a card reader system selectively interfacing with medical smart cards having healthcare information stored thereon, and credit cards; a biometric authentication system including a biometric fingerprint sensor; a high definition camera operated to capture images of individuals using the electronic kiosk; input devices for inputting and navigating through data, and a machine readable storage medium including medical service application software stored thereon that when executed on the computer system displays an interactive program on the interactive touch screen, where the program comprises menus, links, tabs, and icons, associated with managing the healthcare information, and allowing a user to selectively read healthcare information stored on the medical smart card or to selectively write healthcare information to the medical smart card when the medical smart card electrically communicates with the card reader system and when the biometric authenticating system correctly authenticates a fingerprint signature of an authorized user.

These and other advantages of the invention will be further understood and appreciated by those skilled in the art by reference to the following written specifications, claims, and appended drawings.

BRIEF DESCRIPTION OF THE DRAWINGS

The invention will now be described, by way of example, with reference to the accompanying drawings, in which.

Like reference numerals refer to like parts throughout the various views of the drawings.

DETAILED DESCRIPTION OF THE INVENTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Figure 1:
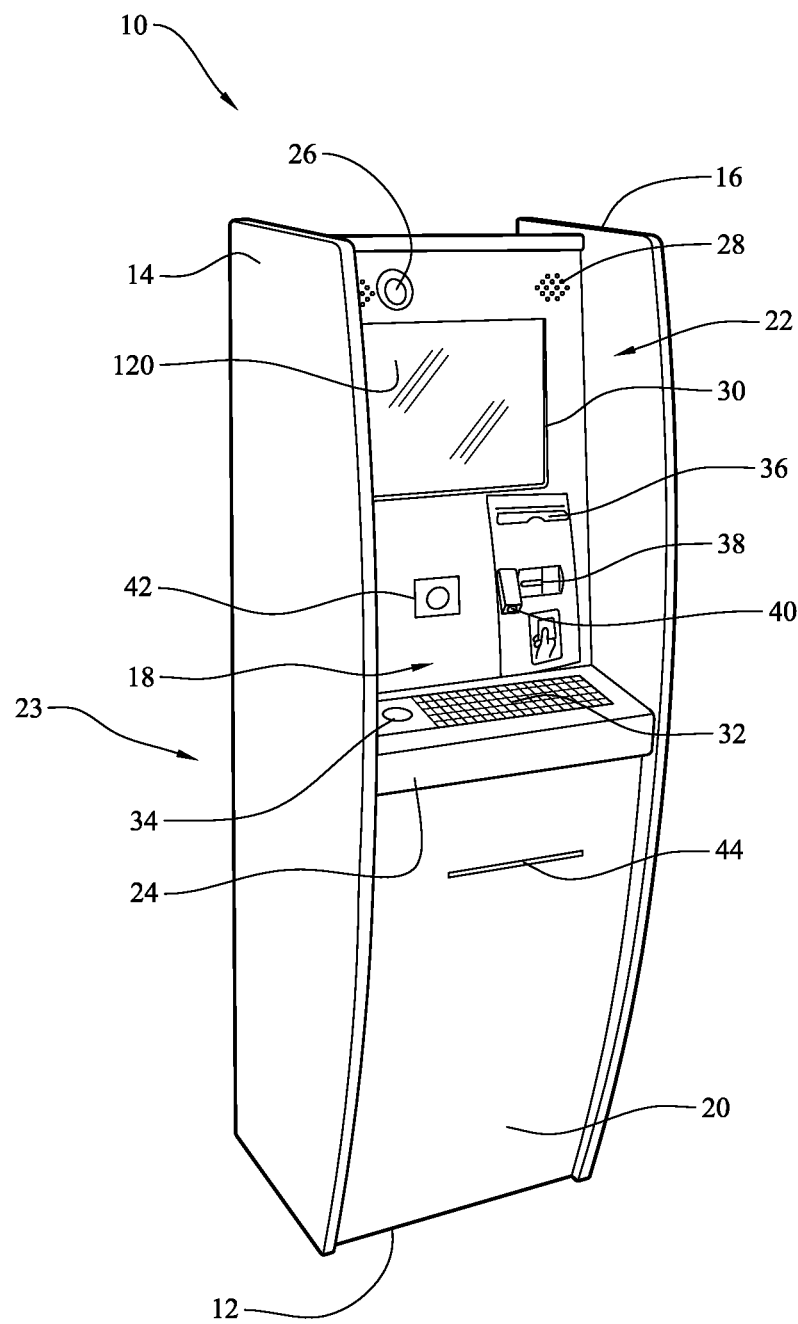
FIG. 1 is a perspective view of an electronic registration kiosk, in accordance with the present invention.
Figure 2:
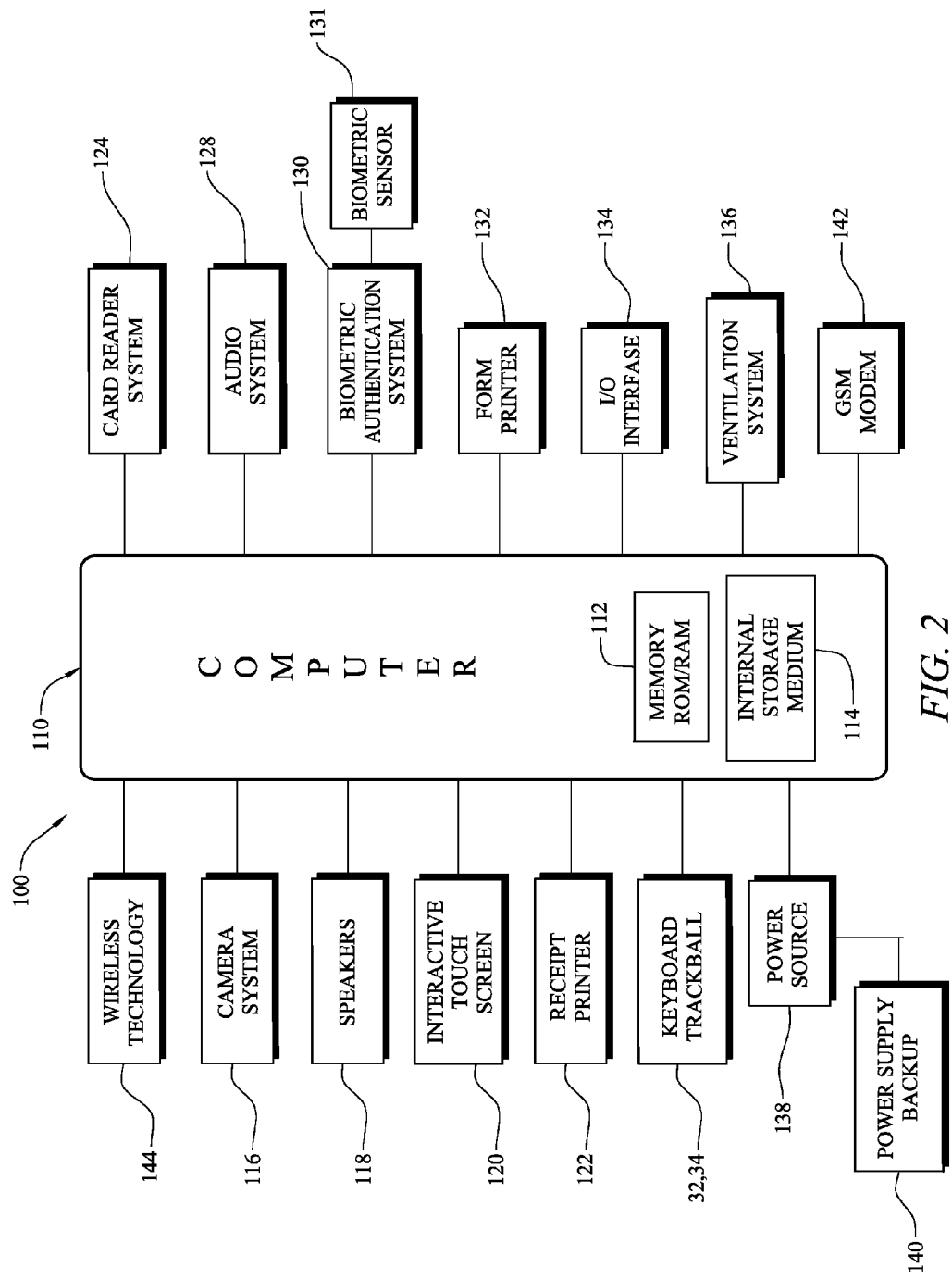
FIG. 2 is a block diagram of the components of the electronic registration kiosk of FIG. 1, in accordance with the present invention.

FIGS. 1 and 2 show a perspective view, and a block diagram of components, respectively, of an electronic registration kiosk (hereafter referred to as registration kiosk), in accordance with one embodiment of the present invention. The structural framework of the registration kiosk 10 includes a base 12, two sidewalls 14, 16 attached to and extending vertically upwards from the base 12, a central panel 18, a front panel 20, and a lateral shelf 24. The central panel 18, front panel 20 and lateral shelf 24 are disposed between sidewalls 14 and 16. As seen in FIG. 1, central panel 18 is setback a distance from the front, longitudinal edges of sidewalls 14, 16 to define a zone of privacy, generally denoted at 22. The zone of privacy 22 provides a level of comfort and security to individuals using the registration kiosk 10. The structural elements are assembled together to form a chamber for securely housing a computer system and electronic components and systems, necessary for operating the registration kiosk 10. A rear panel 23 is attached to the back of the kiosk 10 via, hinges, to provide controlled access to the operative system components of the kiosk 10. Rear panel 23 may include vents to allow heat and air to circulate in and out of the kiosk 10 to help dissipate heat generated by the computer system and operating components. Preferably, rear panel 23 includes a combinational or keyed lock to deter unauthorized personnel from attempting to access the computer operating systems and other components within the interior of kiosk 10. The base 12, sidewalls 14, 16, central panel 18, front panel 20, shelf 24 and rear panel 23 may all be constructed from wood, plastic, metal or any combination thereof. For example, in one non-limiting example, the central panel 18, front panel 22, and rear panel 23 may comprise aluminum or steel, while the vertically extending sidewalls 14, 16, and shelf 24 may comprise wood. The dimensional configuration of the registration kiosk 10 is selected for allowing young and mature adults to use the operative features of the kiosk 10 with ease and comfort. It will be appreciated that the registration kiosk 10 may come in a number of different structural geometric shapes and sizes. For example base 12 may be round, while sidewalls 14, 16 include square or round columns.

The registration kiosk 10 includes a computer operating system 100 including a computer 110 having a processor, read-only memory (ROM) and read-access memory (RAM) 112, and internal storage 114 such as an internal hard drive for storing information, application software, operating programs and the like. The computer 110 is electrically coupled to a number of different operating components or systems, as better illustrated in FIG. 2. The computer system 100 may comprises one or more well-known computers such as a Dell® computer having sufficient processing speed and memory.

A camera aperture 26 is formed within a top section of the central panel 18 to expose a high definition (HD) digital camera 116. High definition camera 116 includes or is electrically coupled to a camera processing unit for capturing, processing and recording activity associated with the use of the registration kiosk 10. As with many ATM machines, digital camera 116 also provides a tool for recording suspect activity of persons who are using the kiosk 10. Camera processing unit may include removeable digital storage, a video or digital recorder and processor, or can be configured to capture still images. The digital storage may include an electronic card, USB flash stick, external hard drive or other well-known storage devices. The high definition camera may include infrared technology or night vision technology for capturing images at night. Alternatively, the registration kiosk 10 may include a lighting system (not shown) that is selected and situated to illuminate the central panel 18 and keyboard area to provide light to users at night. The lighting also provides sufficient illumination for the camera system 116 to operate at night.

With continued reference to FIGS. 1 and 2, central panel 18 includes a plurality of speaker holes 28 formed within the central panel 18 and associated with audio speakers 118 provided within the registration kiosk 10. The audio speakers 118 may comprise mono or stereo speakers and are used to provide audible information to user's such as directions, instructions, or other information. Audible volume, of speakers 118, may be adjustable via, hardware or software. For example, a potentiometer may be included within the registration kiosk 10 to increase or decrease the volume.

A large square-shaped window 30 is formed in the central panel 18 for providing viewing accessibility to a large, interactive touch screen 120 that is securely mounted within the registration kiosk 10. The interactive touch screen 20 permits users to interface with kiosk 10 by directly touching the screen without the need for using a keyboard 32 or trackball 32. Medical management application software is executed, via computer 110, to display icons, tabs, links, and menus on the interactive touch screen 120 for allowing users to interact with the application software when managing medical healthcare information and services. The interactive touch screen 120 may include a liquid crystal display (LCD), a cathode ray tube (CRT), a touch screen monitor, or any other suitable display unit including a color or chromatic display. Touch screen 120 may comprise any touch technology including resistive, surface wave, or capacitive.

One alternative method of interacting with the registration kiosk 10 is provided by a keyboard 32 and a trackball 34 or computer mouse. The keyboard 32 and trackball 34 are used for inputting or selecting data, and navigating and/or scrolling through data screens, forms, or other information displayed on the interactive touch screen 120. Preferably, keyboard 32 comprises a traditional keyboard having standard function keys, however, particular keys associated with designated functions may be included. For example, there may be keys designated to form a particular function like printing a particular form, making a payment or ordering a medical smart card. Each of the keyboard 32 and trackball 34 is preferably secured within or on the lateral shelf 24. Both the keyboard 32 and the trackball 32 may include a water-resistant or water-repellant covering for protecting the keys and ball from damage as a result of the keys and ball being exposed to water or other liquids. This feature may prove to be beneficial where individuals using the registration kiosk 10 are carrying drinks.

The registration kiosk 10 includes a central interface area located in the central region of the kiosk 10 for comfortably allowing users to interface with the kiosk 10 when applying for a medical smart card, or managing healthcare information and services. Located in central interface area of kiosk 10 is a receipt printer slot 36 that is operatively associated with a receipt printer 122. The receipt printer 122 is operated by computer 110 to provide hard copies of receipts evidencing payments made using credit cards, charge cards, or banking accounts. Payments are made pursuant to member service provider fees. The receipt printer 122 may also be adapted to provide information or data relating to a variety of different transactions. For example, such information may include, but is not limited to, the times and dates when information was processed, the type of accounts or databases a card member accessed, confirmation of prescription refills provided, notifications of system changes or alerts, notifications of changes or additions to member provided services, or other information relating to managing healthcare information or services. The receipt printer 122 may include a color, or black and white ink, and may comprise a dot-matrix printer or laser printer. The receipt printer 122 is easily accessible for maintenance via, the rear panel 23 of the registration kiosk 10.

As seen in FIG. 1, a card reader slot, designated at 38, is also provided in the central panel 18 for receiving medical smart cards, credit cards or charge cards. Card reader slot 38 is operatively associated with a card reader system 124 that includes a contact card reader and a contactless card reader. Computer 110 electrically communicates with the card reader system 124 to control the operation of the card reader system 124 by processing data signals and executing routines, instructions and software programs that are generally stored in memory 112. In one embodiment, card reader system 124 includes a card sensor and necessary electronic components, and circuitry needed for electrically interfacing with contact smart cards and/or credit cards. Such cards generally include electrical contacts (or contact pad) disposed on the card for electrically connecting with electrical contacts located in the card reader system 124. When a contact smart card is inserted within card slot 38, contact card reader 124 communicates with the card and reads the information stored on the card. Computer 110 processes the information and the information and data is sent to the interactive touch screen 120 for viewing. Card reader system 124 may also include a magnetic head reader or a bar code reader for reading information stored on cards having a magnetic stripe or bar code.

Card reader system 124 is also used to interface with credit cards or other charge cards for processing financial payments or transactions. Registration kiosk 10 is configured to interface with a credit card service provider, or credit card clearing house via, a network connection that may include cable, telephone, and satellite. In one non-limiting example, registration kiosk 10 can be configured to communicate with a credit card clearing house for processing credit card payments using an internet network. In one alternative embodiment, registration kiosk 10 may also include a bill acceptor slot disposed in the central panel 18 and operatively associated with a bill acceptor for accepting currency in paper form. A user may wish to pay for member provided services or a medical smart card by using paper cash including ones, fives, tens or twenty dollar bills.

In one alternative embodiment of the present invention, the card reader system 124 may also include a contactless card reader. The contactless card reader typically includes a transmitting or reception antenna (not shown) for transmitting and receiving data, and reader circuitry, including cryptography module(s) for providing encryption/decryption protocol, coding/decoding circuitry, modulating/demodulating circuitry, and any additional electronic components and circuits needed for communicating with contactless smart cards. Because security of information is a prime concern, communication between the card reader system 124 and contactless smart cards is enhanced through an encoding or encryption process undertaken by an encryption/decryption protocol. In one embodiment, the encryption process of electronic data is performed using a process or algorithm (generally referred to as a cipher) such as Advanced Encryption Standard (AES 256). The Advanced Encryption Standard includes ciphers based on symmetric key algorithms (private key cryptography). Operating software or hardware based instructions, programs or libraries supporting advanced cryptographic algorithms may be implemented to increase security. Thus, the registration kiosk 10 includes a card reader system 124 for use with contact cards, contactless cards, and credit cards. For added convenience, a contactless smart card reader symbol (not shown) may be located anywhere on the central panel 18 for alerting users that kiosk 10 is compatible for use with contactless cards.

To accommodate individuals having certain disabilities, such as blind people, the registration kiosk 10 includes an audio access port 40 for electrically interfacing ear phones, head phones or the like to an audio system 128. The audio access port 40 is situated on the central panel 18 and may be marked to identify the service. The audio system 128 is designed to provide audible instructions, explanations, data, and information, including but not limited to, how to apply for a medical smart card, how to manage healthcare information using an already existing medical smart card, how to request prescription refills, or provides general information about the medical application program and services offered through the kiosk 10.

The registration kiosk 10 provides secure access control to information stored on medical smart cards by including biometric authentication. Registration kiosk 10 includes a biometric authentication system 130 including a biometric sensor 131 and biometric signature reader for capturing biometric signatures of authorized users. In the preferred embodiment, the biometric sensor 131 comprises a fingerprint sensor, however, other forms of biometric technology may be implemented such as a palm, speech or retinal recognition. The biometric sensor support 42 is provided on central panel 18 to securely retain biometric sensor 131. A biometric signature database including biometric signatures of authorized users is stored in memory 112 in kiosk 10, on an application server, or in an external database that is electrically coupled to the registration kiosk 10. Authorized biometric signatures are compared to fingerprint signatures captured by the biometric reader and use access to the kiosk 10 is granted if the captured fingerprint signature correctly matches the stored biometric signature of an authorized user. Biometric signatures may be stored in a database upon when a user initially registers for a medical smart card.

In one alternative embodiment, camera system 116 may also be used to provide a two-tier authentication level of security. For example, a camera system 116 may be used to capture the image of a user, and compare the captured image with images of authorized users that are stored in an authorized user image database. The increased level of authentication provides enhanced security to information stored on a medical smart card, or to information stored on an application server, or an external database.

With continued reference to FIGS. 1 and 2, the registration kiosk 10 also includes a form printer slot 44 formed in the front panel 22. The form printer slot 44 corresponds to a form printer 132 that is used to print application forms, healthcare directive forms, authorization to treat forms, service agreement forms, immunization forms, HIPPA privacy statements, or other forms, contracts or agreements relating to medical healthcare of a medical smart card holder. Preferably, form printer 132 prints forms having an 8½×11 format though other formats may be implemented. Form printer 132 may include color, or black and white ink, and like the receipt printer 122, is accessible for maintenance or repair via, rear panel 23. Both form printer 132 and receipt printer 122 may include replaceable or refillable toner or ink cartridges. Paper for both printers 122, 132 can be refilled via, rear panel 23.

An input/output (I/O) interface 134 may be included within registration kiosk 10 for electrically interfacing or connecting the kiosk 10 to a variety of external devices or networks. The I/O interface 134 may include a telephone modem and connection, routers and connections, a cable modem and connection, universal serial bus (USB) and/or Ethernet ports, parallel or serial connectors, HDMI connections, power connections, earphone or microphone jacks, and other electrical connections needed for interfacing with electronic devices. In one example, the registration kiosk 10 may be connected to an external devices or network, such as data storage device, a printer, a keyboard, the internet, or to other kiosks or card readers. The I/O interface 134 may be situated within kiosk 10, located on the rear panel 23, or disposed anywhere about sidewalls 14, 16. The I/O interface should be easily accessible.

A ventilation system 136 is implemented to help dissipate heat generated from operating system components located within the registration kiosk 10. The ventilation system 136 may include one or more electric fans controlled by computer 110 to forcibly circulate air in and out of the kiosk 10. A plurality of vents (not shown) may be formed anywhere within sidewalls 14, 16, rear panel 23, or front panel 22 to direct the circulated air out through designated vents. Temperature sensors may be placed within the housing of the kiosk 10 to sense the internal temperature, and to activate the ventilation system 136 when the temperature reaches a predetermined upper limit.

Registration kiosk 10 is powered, via a power supply 138 which includes transformers, AC/DC converters, voltage regulators, rectifiers, fuses, and filters needed to provide clean, stable power to the computer system 100 and other electronic components, circuits and systems of kiosk 10. In a preferred embodiment, kiosk 10 is configured to connect to a 110 volt AC power supply outlet. The registration kiosk 10 of the present invention also includes the benefit of a backup power supply 140. The backup power supply 140 is used to power the kiosk 10 in the event primary power supply 138 fails. The backup power supply 140 may comprise one or more rechargeable or replaceable batteries. The backup power supply 140 includes electrical components to quickly, and effectively switch from power supply 138 to the backup power supply 140 in the event of a power failure.

In the preferred embodiment, the registration kiosk 10 includes a computer readable storage medium which can store data that is accessible by a computer, or has access to a computer readable storage medium. Medical management application software and programs is/are stored on the computer readable storage medium that when executed displays an interactive program on the interactive touch screen 120. The interactive program comprises a plurality of different menus, information screens, links, icons, tabs, and task bars configured for managing healthcare information and services of individuals. For example, the medical application software provides a home page menu including user viewable files, documents or information associated with information relating to, the medical management service system, making payments, a medical smart card registration process, help menus for using the kiosk and medical smart card, printing forms, logging into and out of member accounts, scheduling medical appointments, requesting prescription refills, managing, adding, and editing medical healthcare information, and other member provided services and information.

The computer readable storage medium may include CD-ROMs, optical disks, floppy diskettes, read-only memories (ROMS), random access memories (RAMS), erasable programmable read-only memories (EPROMS), EEPROMs, magnetic or optical cards, flash memory cards, servers, processors or microprocessors with memory, hard drives, computers, magnetic cassettes, digital video disks, or other types of machine-readable mediums suitable for storing electronic instructions, programs or application software. Alternatively, the methods may be performed by a combination of hardware and software.

The medical application software of the present invention provides an avenue for selecting, amending, viewing, printing, adding, deleting, updating, and scheduling medical information and services. In one embodiment of the present invention, the application software is configured to provide a plurality of menus, icons, links, and tabs that are associated with collecting and managing information, including but not limited to the following:

1. User Demographics: Includes personal profile information of a subscriber such as contact addresses, numbers and information, social security information, insurance information, religious preferences, employer information, vaccine or immunization administration record, and the like;

2. In Case of Emergency Contacts (ICE): Includes information pertaining to individuals that a subscriber wishes medical personnel to contact in the event of an emergency. The ICE information includes names, addresses, telephone numbers, email addresses, or other contact information of primary, secondary and tertiary contact individuals;

3. Physicians and/or Specialists: Includes names, addresses, and contact information of a subscriber's primary care and specialist care physician, the hospital or clinic associated with the physician or specialist, and the like. For example, the name and contact information of a cardiologist, proctologist, or ophthalmologist may be included;

4. Current Medical Conditions: Subscriber related information regarding historical or present medical conditions or diagnosis may be listed herein. For example, information indicating that a subscriber suffers from a particular illness such as diabetes, high blood pressure, or cardiovascular disease may be includes. Also whether the person has a pace maker or an insulin pump, and whether the person suffers from any allergies, requires particular treatment, or is unable to tolerate certain medications, and the like;

5. Information of Historical Procedures: Includes information pertaining to medical procedures a subscriber may have received in the past. The information includes materials associated to medical procedures conducted such as any surgeries, related medical scans, colonoscopy, chemotherapy, and the like;

6. Advance Directives: Provides a list of wishes regarding health care and life-saving techniques often employed by Emergency Medical Technicians, physicians, nurses or other medical personnel during an emergency. The system retains a signed and notarized copy of a subscriber's directives. Evidence of a subscriber's wishes can include, but is not limited to, a Living Will, a power of attorney, a contract agreement, an authorization for emergency medical care, or an authorization to treat. An authorization to treat and a service agreement is subject to HIPAA, the American Recovery and Reinvestment Act (ARRA), and state and local privacy laws. A member may amend or replace any directive by providing a new document. All replacement documents must be signed, notarized and sent to the card administration office. Other documents such as donor information forms may also be included;

7. Prescriptions and Over the Counter (OTC) Medicines: Includes information or data regarding the historical, present or historical and present use of prescription medicine, and over the counter medicine including the amount, brand, dosage, and scheduled times for taking the medicines or prescriptions; and 8. Web Documentary Library: Includes documents and forms such as a Service Agreement, an Authorization to Treat, Advanced Directives, an Authorization for a Dependent Child, a School Immunization Form, a Traveler Profile, a HIPPA Privacy Statement, a Power of Attorney, a Living Will, or any other medical information such as MRI or CT scans, reports, lab or test results or reports, results of blood work, samples taken or provided, and the like.

The application software of the present invention may include a maintenance alert program designed to notify service administrators of possible problems associated with the registration kiosk 10. For example, the maintenance program may alert administrators that each printer is low in paper, that printer ink is low, that particular kiosk components have failed, provide internal temperature readings of one or more registration kiosks 10 and alert of high temperature readings, provide notification of suspect activity when using kiosk 10, or that a kiosk 10 is off line.

Fees in providing member services are accessible by individuals for review using any registration kiosk 10. For example, a fee structure may be implemented to cover member services that include: providing a medical smart card, managing healthcare information, and requesting prescription refills. In one non-limiting example, an initial fee of $49.95 may be provided with a yearly renewal rate of $29.95. The application software may provide an icon or tab associated with a fee layout or fee plan(s) to inform individuals of applicable fees. A user may simply interact with the touch screen 120 to view the prescribed fees involved.

The registration kiosk 10 preferably includes a secure Global System for Mobile Communication (GSM) connection. A GSM modem 142 is electrically connected to computer 110 to allow the computer 110 to communicate over a mobile network. The GSM modem 142 provides mobile internet connectivity and can be used for sending and receiving SMS and MMS messages.

Figures 3, 4:
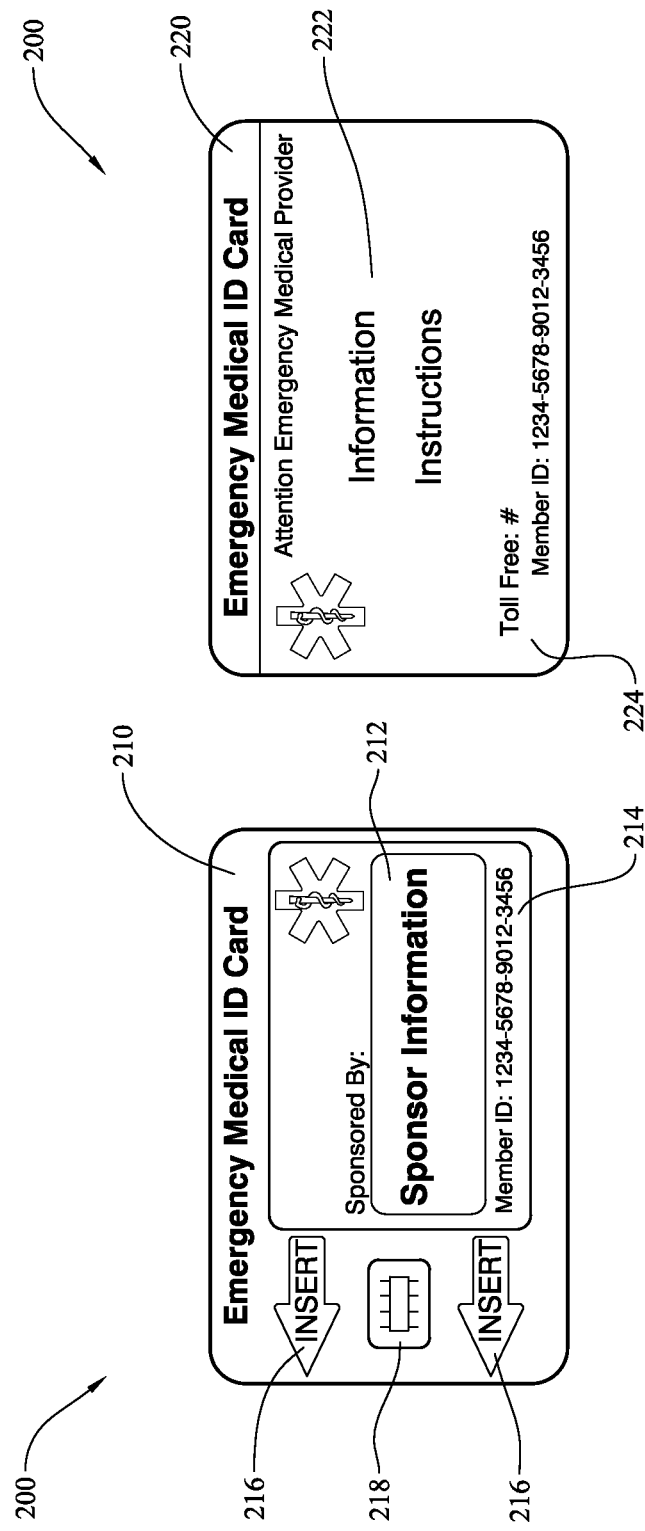
FIG. 3 is a front view of a medical smart card, in accordance with one embodiment of the present invention.
FIG. 4 is a back view of the medical smart card of FIG. 3, in accordance with one embodiment of the present invention.

The registration kiosk 10 of the present invention is made accessible to individuals who wish to apply for a medical smart card. A medical smart card can provide vital medical information about the card holder to medical service providers in the event the card holder cannot communicate. Medical smart cards can be used with registration kiosks 10 or other card readers to view medical information that is stored on the card. One exemplary form of a medical smart card 200 is shown in FIGS. 3 and 4. The term "medical smart card" as used herein refers to any one of a contact card or a contactless card. As a contact card, medical smart card 200 includes a memory chip or integrated circuit that is coupled to electrical contacts or an electrical pad that interfaces with electrical contacts in contact card reader system 124. As a contactless card, smart card 200 includes a smart chip or integrated circuit electrically coupled to an antenna adapted for receiving and/or transmitting data to the card reader system 124.

Medical smart card 200 includes a pocket-sized card fabricated from a plastic material such a polyvinyl chloride. As seen in FIG. 3, the front side 210 of medical smart card 200 includes a central sponsor region 212 dedicated for providing sponsorship information. Sponsor information may include the name or title of a business, facility, department store, pharmacy, or any other business enterprise that promotes or encourages the use of the registration kiosk 10 for managing healthcare information and services. Contact information relating to the sponsor such as business address, phone numbers or internet website addresses may also be provided adjacent the sponsor identification. For example, a registration kiosk 10 that is situated at a particular department store would include medical smart cards 200 that include sponsorship information about that particular department store printed in the sponsorship region 212 of the card.

Each medical smart card 200 includes a member identification number 214 printed on the front 210. The member identification number 214 is a number that is uniquely assigned to each person upon completing the registration process. A number of orientation indicators, such as a pair of arrows, designated at 216 are included on the face of the medical smart card 200 for indicating the proper orientation and handling of the medical smart card 200 when using inserting the smart card 200 into the card reader slot 38 of kiosk 10. Card 200 includes a storage device 218 such as a memory chip, integrated chip, smart chip, a microprocessor, or any combination thereof. Card 200 may include an integrated antenna that is electrically coupled to the chip. Storage device 218 is used for storing medical healthcare information.

FIG. 4 shows a back side view of the medical smart card 200. In one non-limiting embodiment, instructions and supplemental information 222 is printed on the back 220 of the smart card 200 to alert emergency medical providers that vital life-saving information of a patient member is stored on the card 200 and that such information is accessible via, a card reader. In the event the medical service provider does not have access to a card reader, member medical information may be obtained by following the instructions printed on the back 220. The instruction may include information directing attending medical personnel to contact member services to acquire patient healthcare information. Further a telephone number 224 may be included to provide contact information in the event medical service provider, who does not have access to a card reader, wishes to access the information stored on the smart card 200. Upon request, the medical healthcare information of a patient can be faxed to a hospital, clinic, or designated location. Other related information may also be printed on the back 220 of the smart card 200 such as email addresses, website addresses, fax numbers, or other contact information or resources. Instructions, directives and alerts may be marked in bold, dark lettering allowing service providers to quickly and easily view the information.

As a security measure, medical smart card 200 may include one or more passwords or PIN numbers embedded within the storage device 218 to increase access security. In addition, a picture of a card holder can be stored on the card. The cardholder's picture can be viewed by authorized personnel to determine the correct identity of the card holder when providing medical care or granting access. The picture stored on the card may also be compared to the picture captured by the camera system 116 to provide security.

The electronic kiosk 10 of the present invention is made accessible to both potential and existing members by placing registration kiosks 10 in various locations, preferably in high traffic areas. Registration kiosks 10 may be placed in department stores, pharmacies, shopping centers and malls, in clinics, hospitals, and other medical service provider locations, retail stores, grocery stores, convenient stores, offices, and the like.

Individuals will access to a number of kiosks 10 located at various businesses and commercial entities. Generally, a service web home page is displayed on the interactive touch screen 120 of the registration kiosk 10. A potential member can easily navigate through the registration or application process by accessing icons, menus, and tabs that are presented on the interactive touch screen 120. The individual can interact directly with the touch screen 120 to make the appropriate selections, or use the keyboard 32 and trackball 34.

Using a registration kiosk 10, an individual may register to receive a medical smart card 200. To being the registration process, an individual places a finger on the biometric sensor 131 to allow the biometric authentication system 130 to capture a biometric fingerprint signature of the registrant. The management service provider stores the fingerprint signature in a biometric signature database that is located within the registration kiosk 10, or is accessible over a network connection. The camera system 116 operates to capture an image of the registrant as well during the registration process.

The individual enters personal profile information such as name, contact information such as address, phone numbers and emails. During the initial registration process, the person is not required to enter all healthcare information at one time in order to receive a medical smart card. However, if the person wishes to do so, the individual may continue to enter his or her medical healthcare information, if desired. The type of medical information entered may include, but is not limited to, in case of emergency contacts, information about physicians/specialists, current medical conditions, and procedures, prescriptions and over the counter medicine used, and any other medical information. A message indicating that the medical information entered will be verified by the individual's doctor is provided to the registrant.

Through a web document library, various forms may be obtained via, form printer 132. Examples of such forms include but are not limited to, a Service Agreement, a Privacy Agreement, Health Insurance Portability and Accountability Act release, DNR forms, and any other directives or forms. Through the home menu page of the application software, an individual may select healthcare related forms and print the forms out. The printed forms are forwarded through form slot 44 and are completed, properly notarized, and returned to member service provider administrator for proper processing and storage on a smart card 200.

Upon registration, the individual may insert a credit card in the card reader system 124 to pay necessary fees as provided in accordance with a fee schedule. A receipt, evidencing the paid transaction, is printed, via, receipt printer 122, and a hard copy of the receipt is forwarded through receipt slot 36.

The healthcare information entered by the individual is processed and stored. The healthcare information may be transferred to a medical smart card 200 at a preferred date and time. The medical software application program of the present invention may provide a registrant with a choice as to where to pick up a medical smart card 200. For example, a plurality of icons or tabs may provide the registrant with alternative locations where to physically acquire a medical smart card 200 such as in a doctor's office, at a pharmacy, at a particular store or the like. The registrant can simply visit the designated location and pick up the medical smart card 200. Alternatively, the registrant may pick up a medical smart card 200 where there is a card dispensing kiosk for dispensing medical smart cards 200. Thus, after the registration process is completed, a medical smart card 200 is activated and can be picked up at a doctor's office, at a pharmacy or other establishment that participates in the provided member services, or at a medical smart card dispensing kiosk.

In addition, a cardholder can access a registration kiosk 10 anytime for viewing, editing and printing healthcare information stored on an activated medical smart card 200 or for printing medical directive forms. To access healthcare information already stored on an activated medical smart card 200, a user simply inserts the medical smart card 200 into the card reader slot 38 and places a finger on the biometric sensor 130. Biometric authentication system 130 processes the fingerprint signature, and compares the fingerprint signature with acceptable fingerprint signatures stored in a biometric signature database. If the biometric fingerprint signature of the card member matches an authorized fingerprint signature stored in the biometric signature database, the card member is granted access to the healthcare information stored on the smart card 200. Further, the camera system 116 captures the image of the card member while the card member stands in front of the registration kiosk 10. The captured image may be compared to previously stored images, and if a match is satisfied, the card member is granted access to the healthcare information stored on the medical smart card 200. Thus, in one embodiment, registration kiosk 10 may provide a two-tier level of authentication to provide secure access control to healthcare information stored on the medical smart card 200 by requiring biometric authentication and image authentication.

In one alternative embodiment, the registration kiosk 10 of the present invention may require yet another level of authentication. An additional level of authentication may require a medical service provider identification number or password to prevent card members from altering critical medical information without the knowledge and consent of a reviewing physician. For example, if vital, critical medical information needs to be amended, added or deleted, registration kiosk 10 may require another level of authentication be satisfied before making such changes. A physician may be required to enter a user ID number that was previously assigned to him or her. The assigned user ID number is compared to authorized user ID numbers stored in an authorized user ID database. If the assigned user ID number correctly matches an authorized user ID number, the authentication process is satisfied and the physician is granted access to healthcare information stored on medical smart card 200 and allowed to make critical changes to a patient's medical record. Physician user ID authentication helps prevent cardholders from altering or falsifying medical information.

The registration kiosk 10 also allows cardholders to manage healthcare services such as requesting prescription refills. A participating member may access a prescription refill menu provided on the home page menu of the registration kiosk 10. To initiate the process, a member inserts the medical smart card 200 in card reader slot 38 of the kiosk 10, and navigates through the application program to access the prescription refill menu. The prescription refill menu presents the member with several questions. For example, a member may be asked whether the refill request is for the member or a member's dependent. Further, a list of active prescriptions may also be presented to the member for proper selection. For example, if the member has two current prescriptions that are still enforceable, a list of medications may be provided where the list includes the names, brands, dosages and number of refills remaining. Using either the interactive touch screen 120, keyboard 32, or trackball 34, the member can make the proper selection. A confirmation of the member's selection is subsequently provided to the member for review and acceptance.

Authorized personnel at designated doctor's office can review the prescription refill request and determine whether the request is viable in light of authorized refills remaining. If so, the prescription request will automatically be sent to a participating pharmacy. A text message or email is subsequently sent to a member's device notifying the member that the refill is ready for pick up. During the registration process for requesting a medical smart card 200, or anytime thereafter, a member may access a registration kiosk 10 to provide the requisite contact information regarding a member's device such as a pager, computer, tablet, or phone. The member provides the email addresses or telephone numbers where prescription refill confirmation is to be sent.

A healthcare management information and service system network may be provided where a plurality of registration kiosks 10 are electrically connected to an application server via, a network. The system network allows a plurality of registration kiosks 10 to be operated in a client-server configuration to provide medical service providers and existing members' access to medical information, databases, libraries, or web pages provided from a web-based server, or to permit new members to register for a medical smart card 200. Any conventional web browser can be used with the registration kiosk 10 to display and manipulate data on web pages. The central management of all registration kiosks 10 allows for single, application software updates without the need of having to access each individual kiosk 10 to make the necessary software updates. Application software is tailored to include a plurality of drop down menus, function specific icons, taskbars, tabs, and user accessible and viewable interlinked HTML or XML files or documents. Conventional website design techniques may be used to create an on-line medical web application software program.

One or more application servers including the requisite memory and processors may be used to store and operate medical application software programs, instructions, computer code, and other processing features. The application server may include one or more internal databases, or be electrically coupled to one or more external databases.

Each registration kiosk can access the application server via, a wired or wireless network. Each registration kiosk 10 may include any type of wireless transmission technology 144, including, but not limited to, Wi-Fi, 2G, 3G, 4G, 5G, Blue Tooth or Wi Max. Possible communication networks that may comprise a network or be otherwise part of the system, includes but is not limited to internet, intranet, a local area network (LAN) or a wide area network (WAN), a telephone line, cable, or a satellite communication link. Thus, the applicable medical application software, programs, algorithms, and databases may be loaded on a computer readable medium that resides within each registration kiosk 10, or alternatively, the medical application software may reside on an application server 302 that is accessible by a plurality of registration kiosks 10 over a wired or wireless network. The client-server configuration permits a number of registration kiosks 10 to be placed in a variety of different locations where each kiosk connects to an application server 304 over an internet connection. Each kiosk 10 may include a GSM modem 142 to communicate over a mobile network.

Figure 5:
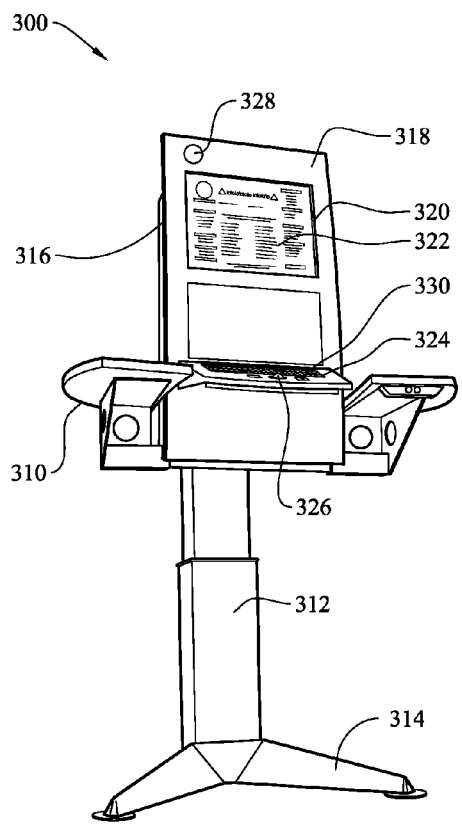
FIG. 5 is a perspective view of a registration kiosk, in accordance with another embodiment of the present invention; and finally.

Turning now to FIG. 5 there is shown a registration kiosk, in accordance with an alternative embodiment of the present invention. Registration kiosk 300 provides an alternative version of the floor kiosk of FIG. 1, and includes a table 310 coupled to a vertically adjustable column 312 that is supported by a base 314. Base 314 may include individually threaded feet for leveling the kiosk 300 or, alternatively, a set of lockable wheels (not shown) for transporting the kiosk 300 from one location to another. The vertically adjustable column 312 conveniently allows a user to raise or lower an operating unit 316.

Operating unit 316 includes a housing for enclosing a computer system 100 therein. Unit 316 includes a front panel 318 having a square shaped opening 320 for providing access to an interactive touch screen 322. As with the registration kiosk 10, the medical management application software is executed, via computer 110, to display icons, tabs, links, and menus on the interactive touch screen 322 for allowing users to interact with the application software when managing medical healthcare information and services. The interactive touch screen 322 may include a liquid crystal display (LCD), a cathode ray tube (CRT), a touch screen monitor, or any other suitable display unit including a color or chromatic display.

Registration kiosk 300 further includes a keyboard 324 and a trackball 326 or computer mouse. The keyboard 324 and trackball 326 are used for inputting or selecting data, and navigating and/or scrolling through data screens, forms, or other information displayed on the interactive touch screen 322. Preferably, keyboard 324 comprises a traditional keyboard having standard function keys, however, particular keys associated with designated functions may be included. The keyboard 324 and trackball 326 are secured to front panel 318 or to table 310.

Registration kiosk 300 may further include a camera 328 associated with a camera system 116 for capturing images of users and a biometric authentication system 330 for providing secure access control to healthcare information stored on an application server or on a medical smart card 200. The kiosk 300 may include a card reader slot 332 associated with a card reader system 124 for interfacing with medical smart cards 200, and a handicapped audio port.

Figure 6:
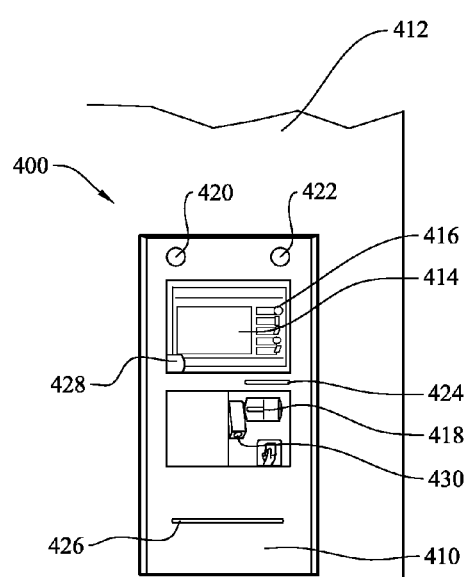
FIG. 6 is a front view of a wall-mountable registration kiosk, in accordance with yet another embodiment of the present invention.

FIG. 6 shows a front view of a wall-mountable registration kiosk, in accordance with another embodiment of the present invention. In this embodiment, the wall-mountable registration kiosk 400 includes an outer face plate 410 securely attached to a vertical wall 412 of a building. Kiosk 400 includes is configured to house a computer system 100 therein. Kiosk 400 includes a display or interactive touch screen 414, input keys 416, and a card reader slot 418 associate with a card reader system 124 for interfacing with medical smart cards 200 to read and view healthcare information stored on the medical smart card 200.

Wall-mountable kiosk 400 may also include a camera 420 associated with a camera system 116, audible speakers 422 electrically connected to the audio process system 128, a receipt printer slot 424 functionally associated with a receipt printer 122, a form slot 426 functionally associated with a form printer 132, a card reader slot 430 associated with a card reader system 124, and a handicapped audio port 430. Kiosk 400 may also require biometric authentication including biometric authentication system 130 electrically coupled to a biometric sensor 131.

Thus, all or selective components of the computer operative system 100 of FIG. 2 can be implemented for use in both registration kiosks 300 and 400. The registration kiosks 10, 300, 400 of the present invention are designed to assist individuals in registering for a medical smart card 200, and in managing healthcare information and services. Registration kiosks 10, 300 may be transported from one location to another, while the wall-mountable registration kiosk 400 is permanently installed in one location.

Registration kiosks 10, 300, 400 can be centrally managed in a client-server configuration, where each kiosk 10, 300, 400 communicates with an application server over a network. The network configuration allows individuals to manage healthcare information and services using a medical application software that is stored on the application server. Alternatively, each kiosk 10, 300, 400 may include a computer operated medium to store and run a medical application software used in managing healthcare information and services, such as applying for a medical smart card 200, managing healthcare information stored on a medical smart card 200, requesting prescription refills, making appointments, and printing medical directive forms. Kiosks 10, 300, 400 may be place in a variety of different locations that are easily accessible to users.

Since many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalence.

We claim:

1. A registration kiosk comprising:
an exhibit housing a computer system and system devices, said computer system including a processor and a memory and electrically communicating with said system devices, said system devices including;
an interactive touch screen;
a first printer for printing receipts, and a second printer for printing healthcare related forms, said first printer associated with a first printer slot, and said second printer associated with a second printer slot;
a card reader system selectively interfacing with medical smart cards including healthcare information stored on said cards, and credit cards;
a biometric authentication system including a biometric sensor for capturing biometric signatures;
a high definition camera system operated to capture images of individuals using said kiosk;
a keyboard; and
wherein said registration kiosk is used to manage healthcare information or services including applying for a medical smart card, printing medical directive forms, and requesting prescription refills, and wherein said healthcare information includes an individual's demographic and profile information, medical emergency contact information, physician/specialist information, medical conditions, procedural medical history, information relating to prescription and over-the-counter medicine, vitamins or supplements, vaccination or immunization historical records, advance directives, medical insurance information, and a photograph of an individual owner of said medical smart card, and wherein said healthcare related forms includes any of service agreements, authorizations to treat, advanced directives, immunization forms, privacy statements, laws and rules, a power of attorney, and a living will.

2. The registration kiosk of claim 1, further including an audio system electrically coupled to said computer system and including one or more speakers associated with speaker holes that are provided in a front area of said exhibit.

3. The registration kiosk of claim 2, further including wireless technology including any one of 2G, 3G, 4G, Wi-Fi, WiMax or Blue Tooth technology, an input/output (I/O) interface situated about said exhibit and including at least one of a universal serial bus (USB) port, an Ethernet port, a TTL port, a serial and parallel port, modem connections, cable connections or telephone line connections.

4. The registration kiosk of claim 3, further including a handicapped audio access port, said audio access port electrically coupled to said audio system and said computer system for providing audible information, data or instructions, and further including a trackball located adjacent said keyboard, a ventilation system, and a backup power supply.

5. The registration kiosk of claim 4, wherein said biometric sensor includes any one of a fingerprint sensor, a palm sensor, a speech recognition system, or a retinal validation sensor, and wherein said biometric authentication system further includes a biometric signature database including biometric signatures associated with a plurality of individuals authorized to use said registration kiosk.

6. The registration kiosk of claim 5, wherein said exhibit includes a base, two vertical sidewalls extending upwards from said base, a central panel, a front panel, a lateral shelf, and a rear panel, wherein said central panel is setback a distance from front longitudinal edges of said sidewalls to define a zone of privacy, and wherein said biometric sensor, said audio access port, a card reader slot and said first printer slot are disposed on or in said central panel between said two vertical sidewalls.

7. The registration kiosk of claim 5, wherein said exhibit includes a table having a left support and a right support, said table attached to a vertically adjustable column, said vertically adjustable column including a base for supporting said kiosk on a horizontal surface, and said keyboard being disposed between said left support and said right support.

8. The registration kiosk of claim 5, wherein said exhibit includes a wall-mountable kiosk having a faceplate with an opening to provide access to said interactive touch screen, said keyboard including a plurality of keys situated about said face plate.

9. A method of registering for a medical smart card and managing healthcare information and services, said method being performed at least partially by a registration kiosk operated by an individual user, comprising the steps of:
operating an application server hosting medical service application software associated with managing individual healthcare information and services, said registration kiosk electrically communicating with said application server over a wired or wireless network;
capturing an image of the individual user using said registration kiosk with a high definition camera comprised in the registration kiosk, and processing a biometric signature of the individual user by a biometric authentication system comprised in the registration kiosk that includes a biometric sensor for capturing biometric signatures; and
receiving information from an individual user to register for a medical smart card, and storing the received information on said medical smart card upon successful completion of a registration process, or selectively interfacing a medical smart card with a card reader system of said registration kiosk to view and manage healthcare information and services when said biometric signature of said individual user is authenticated, said medical smart card including healthcare information including the individual user's demographic and profile information, medical emergency contact information, physician/specialist information, medical conditions, procedural medical history, information relating to prescription and over-the-counter medicine, vitamins or supplements, vaccination or immunization historical records, advance directives, medical insurance information, and a photograph of the individual owner of said medical smart card, and wherein said healthcare related forms includes any of service agreements, authorizations to treat, advanced directives, immunization forms, privacy statements, laws and rules, a power of attorney, and a living will.

10. The method of claim 9, further including the step of receiving a request for prescription refills of medication, and sending a text or email message confirming readiness of said refills.

11. The method of claim 10, wherein the step of processing a biometric signature of the individual user includes the step of reading a biometric fingerprint signature of said user when said user places a finger on said biometric sensor.

12. The method of claim 11, wherein the step of receiving information of an individual user to register for a medical smart card includes the step of entering personal information, or entering personal information and medical information, and wherein the step of receiving information of an individual user to register for a medical smart card further includes a step of paying a predetermined fee with a credit card to complete said registration process.

13. The method of claim 12, further including the step of printing a receipt via a first printer comprised in the registration kiosk, and further including the step of printing healthcare related forms via a second printer comprised in the registration kiosk, said receipt and said healthcare related forms forwarded through a corresponding slot comprised in the registration kiosk.

14. The method of claim 13, wherein said medical service application software provides an interface on a touch screen comprised in the registration kiosk including menus, links, tabs and icons for managing healthcare associated with individual users, said medical service application software being executed on said registration kiosk or accessible to said registration kiosk via, said application server.

15. An electronic kiosk for managing healthcare information and services, said electronic kiosk comprising:
a structure housing a computer system having a memory and a processor and including:
an interactive touch screen;
a first printer for printing receipts, and a second printer for printing healthcare related forms;
a card reader system selectively interfacing with medical smart cards having healthcare information stored thereon, and credit cards;
a biometric authentication system including a biometric fingerprint sensor;
a high definition camera operated to capture images of individuals using said electronic kiosk;
input devices for inputting and navigating through data; and
a machine readable storage medium including medical service application software stored thereon that when executed on said computer system displays an interactive program on said interactive touch screen, said program comprising menus, links, tabs, and icons, associated with managing said healthcare information, and allowing a user to selectively read healthcare information stored on said medical smart card or to selectively write said healthcare information to said medical smart card when said medical smart card electrically communicates with said card reader system and when said biometric authenticating system correctly authenticates a fingerprint signature of an authorized user, said healthcare information including an individual's demographic and profile information, medical emergency contact information, physician/specialist information, medical conditions, procedural medical history, information relating to prescription and over-the-counter medicine, vitamins or supplements, vaccination or immunization historical records, advance directives, medical insurance information, and a photograph of an individual owner of said medical smart card, and wherein said healthcare related forms includes any of service agreements, authorizations to treat, advanced directives, immunization forms, privacy statements, laws and rules, a power of attorney, and a living will.

16. The electronic kiosk of claim 15, further including an audio system including speakers and a handicapped audio access port, and including wireless technology including any one of 2G, 3G, 4G, Wi-Fi, WiMax or Blue Tooth technology, wherein said input devices include a plurality of keys and a trackball adjacent said plurality of keys.

17. The electronic kiosk of claim 16, wherein said structure includes a base, two vertical sidewalls extending upwards from said base, a central panel, a front panel, a lateral shelf, and a rear panel, wherein said central panel is setback a distance from front longitudinal edges of said sidewalls to define a zone of privacy, and wherein said biometric sensor, said audio access port, a card reader slot and said first printer slot are disposed on or in said central panel between said two vertical sidewalls.

18. The electronic kiosk of claim 16, wherein said structure includes a table having a left support and a right support, said table attached to a vertically adjustable column including a base for supporting said kiosk on a horizontal surface.

19. The electronic kiosk of claim 16, wherein said structure includes a wall-mountable kiosk having a faceplate with an opening to provide access to said interactive touch screen, said plurality of keys situated on said face plate.

\* \* \* \* \*